United States Patent [19]

Mirviss

[11] Patent Number: 4,582,903

[45] Date of Patent: Apr. 15, 1986

[54] SYNTHESIS OF UNSATURATED HYDANTOINS WITH AN INEXPENSIVE CATALYST

[75] Inventor: Stanley B. Mirviss, Stamford, Conn.

[73] Assignee: Stauffer Chemical Company, Westport, Conn.

[21] Appl. No.: 641,888

[22] Filed: Aug. 17, 1984

[51] Int. Cl.[4] .................. C07D 413/10; C07D 233/96
[52] U.S. Cl. .................................. 544/139; 544/335; 546/210; 546/278; 548/308; 548/309; 548/311
[58] Field of Search ..................... 548/308, 311, 309; 546/210, 278; 544/139, 335

[56] References Cited

U.S. PATENT DOCUMENTS

| | | | |
|---|---|---|---|
| 2,435,399 | 2/1948 | Livak et al. | 548/309 |
| 2,861,079 | 11/1958 | Britton et al. | 548/308 |
| 4,175,198 | 11/1979 | Gaudette | 548/308 |
| 4,345,072 | 8/1982 | Kleemann et al. | 548/308 |

OTHER PUBLICATIONS

Kirk–Othmer *Encyclopedia of Chemical Technology*, 3rd ed., vol. 12, pp. 694–695.
Wheeler, H. et al., *J. Biol. Chem.*, X, 147–157, (1912).
Johnson, T., *J. Am. Chem. Soc.*, 61, 2485, (1939).
Slater, G., *Can. J. Chem.*, 42, 1768, (1964).
Bond, H., *J. Biol. Chem.*, 175, 531, (1948).
Shabica, A. et al., *J. Am. Chem. Soc.*, 68, 1156, (1946).
Majima, R., *Ber.* 55, 3859, (1922).
Moriya, T., et al., Chem. Pharm. Bull., (Japan), 28(6), 1891, (1980).
Bucherer, T., et al., *J. Prakt. Chem.* 141, 30–43, (1934).
Billek, G., et al., *Monat. Chem.*, 90, 89–95, (1959).
Billek, G., *Monat. Chem.*, 92, 352–360, (1961).
Thielemann, H., *Naturwiss.*, 20(2), 89–95, (1971).

*Primary Examiner*—Richard A. Schwartz
*Attorney, Agent, or Firm*—Paul J. Juettner

[57] ABSTRACT

Alkylidene or arylidene substituted hydantoins are produced by condensation of an aromatic or aliphatic aldehyde with hydantoin in the presence of at least one basic salt of an inorganic acid. The desired products are obtained in high yields.

15 Claims, No Drawings

SYNTHESIS OF UNSATURATED HYDANTOINS WITH AN INEXPENSIVE CATALYST

FIELD OF THE INVENTION

The present invention relates to a method for the production of unsaturated hydantoins. More particularly, the present invention relates to an improved method wherein the condensation of the alkyl or aryl aldehyde with a substituted or unsubstituted hydantoin is carried out in the presence of a basic salt of an inorganic acid to form the corresponding unsaturated hydantoin.

BACKGROUND OF THE INVENTION

It has long been common practice to use hydantoin and substituted hydantoins as precursors and intermediates in the synthesis of amino acids. The use of substituted hydanotins in the synthesis of amino acids such as alanine, methionine, tryptophan and lysine is well documented in the prior art. (Kirk Othmer, Encyclopedia of Chemical Technology, Volume 12, pages 694–695). The recent development of the artificial sweetner aspartame has also focused attention on the use of 5-arylidene substituted hydantoin as an intermediate in the synthesis of phenylalanine, a necessary ingredient in the synthesis of aspartame. The process for carrying out the condensation reaction of an aromatic aldehyde with hydantoin to form these 5-arylidene substituted hydantoins is also well known. (Wheeler and Hoffman, Amer. Chem. J., Volume 45, pages 368–83 (1911). A number of patents report improvements on these methods.

In U.S. Pat. No. 2,861,079, unsaturated hydantoins are produced by reacting aldehydes with hydantoin in an aqueous solution or a solution of a lower aliphatic alcohol containing an equimolar amount of a monoalkanolamine. This method has the disadvantage that, even when water is used as a solvent, large quantities of water soluble expensive amines, such as diethanolamine, are required.

In U.S. Pat. No. 4,345,072, an aromatic aldehyde substituted or unsubstituted in the aromatic nucleus is reacted with hydantoin in the presence of an equimolar amount of at least one ammonium salt of an aliphatic or aromatic carboxylic acid. A disadvantage of this method is that it requires the use of expensive carboxylic acids as solvents. Even if water is used as the solvent, this patent still requires the use of expensive ammonium salts of carboxylic acids. In addition, the process of the U.S. Pat. No. '072 requires the use of a high molar ratio of catalyst to hydantoin to achieve the desired results.

SUMMARY OF THE INVENTION

The process of the invention is characterized by the reaction of an aryl or alkyl aldehyde with a substituted or unsubstituted hydantoin in the presence of a basic salt of an inorganic acid. The process of the invention allows the use of aqueous solvents, eliminates the need for expensive amine derivatives, does not require expensive ammonium salts of carboxylic acids and can be done using a low molar ratio of catalyst to hydantoin. The process of the invention also results in substantially high yields of the desired product in a pure form.

DETAILED DESCRIPTION OF THE INVENTION

The process of the invention is particularly suited for the production of substituted unsaturated hydantoins of the general formula.

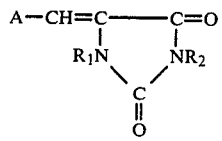

where A is X or Y, and X is an unbranched or branched alkyl or alkenyl group, a cycloalkyl group, a cycloalkenyl group, an alkylthio group, a haloalkyl group, a haloalkenyl group, a hydroxyalkyl group, an aralkyl group, a mono- or dialkylaminoalkyl group, an acylaminoalkyl group, or a mercaptoalkyl group. Preferably the alkyl groups contain 1 to about 20, especially 1 to about 10 carbon atoms, the alkenyl group 1 to about 10, especially 1 to about 5 carbon atoms, the cycloalkyl and cycloalkenyl groups from about 3 to about 15, preferably from about 3 to about 10 carbon atoms. In a given case in the cycloalkyl or cycloalkenyl group, one or more —$CH_2$— units can also be replaced by —O—, —S—, or —NH—, or —C= can be replaced by —N— so that there is present the corresponding heterocyclic ring with about 3 to about 15, preferably from about 3 to about 10 ring atoms. The alkoxy, alkylthio, hydroxyalkyl, mercaptoalkyl, mono or dialkylaminoalkyl and acylaminoalkyl groups contain preferably 1 to about 10, especially 1 to about 6 carbon atoms in the alkyl or acyl groups, and

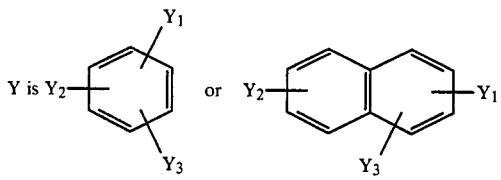

in which $Y_1$, $Y_2$, and $Y_3$ are the same or different and can be X as defined above, hydrogen, halogen, e.g. of atomic weight 9 to 80, a hydroxy group, a nitro group, a cyano group, an amino group, an aralkyl group, or an alkaryl group. Preferably, the aralkyl and the alkaryl groups contain from about 7 to about 15 carbons in the alkylene or alkyl groups. In a given case, two of the groups $Y_1$ to $Y_3$ together can form an alkylene or alkenylene group with from about 3 to about 5 carbon atoms whereby in this case one or more —$CH_2$— units can be replaced by —O—, —S—, or —NH— or —CH= can be replaced by —N=.

$R_1$ and $R_2$ are the same or different and are hydrogen, alkyl, aryl, or amino.

Accordingly, there are employed aliphatic aldehydes having the formula

X—CHO wherein X is as defined above. Non-limiting examples of suitable aldehydes include butyraldehyde, isobutyraldehyde, valeraldehyde, isovaleraldehyde, caproaldehyde, enanthaldehyde, nonaldehyde, cyclobutylaldehyde, cyclopentylaldehyde, cyclohexylaldehyde, furfural, 2-thiophenealdehyde, 2-pyrrolealdehyde, imidazolealdehyde, oxazolealdehyde, 3-indolealdehyde, pyridylaldehyde, pyrimidylaldehyde, malonic acid half aldehyde and monoaldehyde derivatives of dicarboxylic acids.

Non-limiting examples of appropriate aromatic aldehydes having the formula Y—CHO include, benzaldehyde, tolylaldehyde, 4-isopropylbenzaldehyde, 4-hydroxybenzaldehyde, 3,4,5-trimethoxybenzaldehyde, 3-bromo-4-methoxybenzaldehyde, 3,4-methylenedioxybenzaldehyde, 2-hydroxy-4-nitrobenzaldehyde, 4,5-dimethoxy-2-nitrobenzaldehyde, salicylaldehyde, vanillin, 4-phenylbenzaldehyde, 4-benzylbenzaldehyde, 4-fluorobenzaldehyde, 4-dimethylaminobenzaldehyde, 4-acetoxybenzaldehyde, 4-acetaminobenzaldehyde, 4-methylthiobenzaldehyde, and 3,5-dichloro-4-hydroxybenzaldehyde. Additional aldehydes include p-tolylaldehyde, m-tolylaldehyde, 4-chlorobenzaldehyde, 4-hexylbenzaldehyde, 2-allylbenzaldehyde, 4-allylbenzaldehyde, 2-vinylbenzaldehyde, 3-vinylbenzaldehyde, 4-methallylbenzaldehyde, 4-crotylbenzaldehyde, 2-nitrobenzaldehyde, 3-nitrobenzaldehyde, 4-nitrobenzaldehyde, 2-aminobenzaldehyde, 4-aminobenzaldehyde, 4-cyclopropylbenzaldehyde, 2-cyclopropylbenzaldehyde, 4-cyclohexylbenzaldehyde, 2,6-dichlorobenzaldehyde, anisaldehyde, 3-hydroxybenzaldehyde, 2-hydroxybenzaldehyde, 2-hydroxy-4-methylbenzaldehyde, 2-hydroxy-3-methoxybenzaldehyde, veratraldehyde, 2,4-dihydroxybenzaldehyde, 2,5-dihydroxybenzaldehyde, 4-cyclohexenylbenzaldehyde, 4-cyclooctylbenzaldehyde, 4-piperidinylbenzaldehyde, 4-pyridylbenzaldehyde, 4-furylbenzaldehyde, 4-thienylbenzaldehyde, 4-phenylethylbenzaldehyde, 4-sec.butylbenzaldehyde, 4-morpholinobenzaldehyde, 4-isopropoxybenzaldehyde, 2-propoxybenzaldehyde, 3-ethoxybenzaldehyde, 4-hexoxybenzaldehyde, 2-isopropylaminobenzaldehyde, 4-hexylaminobenzaldehyde, 4-diethylaminobenzaldehyde, 4-dipropylaminobenzaldehyde, 4-methylethylaminobenzaldehyde, 3,4-ethylenedioxybenzaldehyde, 4-acetylthiobenzaldehyde, 4-propionoxybenzaldehyde, 4-formyloxybenzaldehyde, 4-butyroxybenzaldehyde, 3,4-tetramethylenebenzaldehyde, 3,4-trimethylenebenzaldehyde, 3,4-dihydroxybenzaldehyde, alpha-napthaldehyde, beta-napthaldehyde, and 3-indenecarboxaldehyde.

In addition, hydantoins substituted at the N-1 or N-3 position can also be used in the condensation reaction. Examples of such hydantoins include, 3-methylhydantoin, 1,3-dimethylhydantoin, 1-phenylhydantoin, 3-benzylhydantoin, 1,3-dibenzylhydantoin and the like.

The inexpensive basic salts of an inorganic acid to be employed in the reaction include ammonium bicarbonate or ammonium carbonate with the bicarbonate being the preferred compound. The basic salt can be derived from any inorganic acid with a $pK_a$ of above 5. For example, basic salts derived from carbonic acid ($pK_a = 10.3$), the bicarbonate of carbonic acid ($pK_a = 6.4$), or the monoacid phosphate of phosphoric acid ($pK_a = 12.4$) can be used.

The basic salt used is dissolved in an aqueous solvent. Other solvents include water/alcohol, or water/glycol(s). Preferably, the aldehyde is added to the solution of catalyst, solvent and hydantoin.

Generally, the condensation takes place at a temperature between about 0° to about 120° C., especially at a temperature of about 10° to about 105° C. The pressure at which the reaction is carried out is atmospheric but superatmospheric pressure can also be used.

The molar ratio of aldehyde to hydantoin can be 0.8 to 1.2. Generally, it is advantageous to employ per mole of hydantoin from about 0.85 to 1.15 moles, especially from about 0.9 to about 1.1 moles of the aldehyde.

Per mole of hydantoin, there is suitably employed an effective amount, ranging from at least 0.10 mole, preferably from about 0.20 to about 1.0 moles, especially from about 0.20 to about 0.6 moles, of the basic salt of the inorganic acid.

The reaction can be carried out on a small scale or a large scale and can be done batchwise or in a continuous fashion. If a continuous reaction is chosen, the reaction is monitored and reactants are added when depleted.

The process can comprise, consist essentially of, or consist of the steps set forth in the stated examples.

COMPARISON EXAMPLE

Similar to the procedure of U.S. Pat. No. 4,345,072, a mixture comprising hydantoin (25 g, 0.25 mole), benzaldehyde (29.3 g, 0.275 mole), ammonium acetate (19.3 g, 0.25 mole) and glacial acetic acid (60 g) were placed in a round bottom flask fitted with stirrer, condenser, thermometer and heating mantle. The white solids became yellow on heating. All the solids dissolved when the temperature reached between 120° C. and 134° C. The mixture was refluxed for one-half hour (125° to 134° C.) and then held at 120° C. for 4 hours with stirring. Solids crystallized out on cooling to room temperature. The solid was suction filtered, water washed and then ethanol washed. After air drying, the yellow orange solid had a weight of 38.0 g for an 81% yield. The melting point of the 5-benzalhydantoin obtained was determined to be 218°–220° C. which corresponds to the melting point reported in BIOCHEM J. 29, 542 (1935).

EXAMPLE 1

The Comparison Example was repeated using 25 g of hydantoin and 29.3 g of benzaldehyde but 125 ml of water was used as a solvent. 9.9 g of ammonium bicarbonate (0.125 mole, 50 mole % of hydantoin) was added with stirring over a period of 10 minutes. A considerable amount of white solid formed. The mixture was stirred at reflux for 4 hours. The reaction mixture was washed as above and 45 g of a white solid determined by UV analysis to be 5-benzalhydantoin was obtained. The theoretical yield based on starting material was 96%. The 5-benzalhydantoin had a melting point of 215°–221° C.

EXAMPLE 2

This Example illustrates that the above process of Example 1 can be adapted to a large scale process. In this variation, large quantities of raw materials were used. 1313 g of 99% pure hydantion (13.0 moles on a 100% basis), 5000 g of distilled water, 257 g of ammonium bicarbonate (3.25 moles) and 1367 g or 12.9 moles on a 100% pure basis of benzaldehyde (1395 g on an actual 98% pure basis) were used. The benzaldehyde was added to the other stirred ingredients over a period of 3 hours at 33°–98° C. with the temperature being gradually increased to the reflux temperature of 98° C. The mixture was stirred at reflux for 6 hours. The light yellow-white solid formed was filtered off and then washed twice with 1 liter of distilled water each wash and then dried on a suction filter. The product was then washed with 1.5 liter of ethanol and then dried on the suction filter. The white solid was forced air dried in an oven and had a weight of 2155 g corresponding to a yield of 89% based on benzaldehyde. The melting point was 219°–222.5° C.

Additional features of the preferred and most preferred features of the invention are found in the claims hereinafter.

What is claimed is:

1. A process for the condensation reaction of an aldehyde with hydantoin to produce an unsaturated hydantoin comprising carrying out the condensation reaction in the presence of at least one basic salt of an inorganic acid.

2. A process according to claim 1 wherein there is employed at least 0.1 mole of the basic salt of the inorganic acid per mole of reacting hydantoin.

3. A process according to claim 2 wherein there is employed from about 0.2 to about 1.0 mole of the basic salt of an inorganic acid.

4. A process according to claim 2 wherein the temperature is 10° to 105° C.

5. A process according to claim 4 wherein the basic salt is a salt of an inorganic acid having a $pK_a$ above 5.

6. A process according to claim 5 wherein the inorganic acid is carbonic acid, the biocarbonate of carbonic acid, or the monoacid phosphate of phosphoric acid.

7. A process according to claim 6 wherein the inorganic acid is carbonic acid.

8. A process according to claim 2 wherein the basic salt is ammonium bicarbonate.

9. A process according to claim 2 wherein the basic salt is ammonium carbonate.

10. A process according to claim 2 wherein the condensation reaction is carried out in an aqueous solvent.

11. A process according to claim 2 wherein the hydantoin formed has the formula

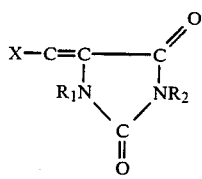

wherein $R_1$ and $R_2$ are hydrogen, alkyl, aryl, or amino and the aldehyde employed has the formula X—CHO 

where X is the unbranched or branched alkyl or alkenyl, cycloalkyl, cycloalkenyl, alkylthio, mono or dialkylaminoalkyl, acylaminoalkyl, hydroxyalkyl, aralkyl, alkaryl, haloalkyl, haloalkenyl, mercaptoalkyl, cycloalkyl having a —CH$_2$ group replaced by —O—, —S—, or —NH—, cycloalkenyl having a —CH— replaced by —O—, —S—, or N.

12. A process according to claim 11 wherein the aldehyde employed is selected from the group consisting of butyraldehyde, isobutyraldehyde, valeraldehyde, isovaleraldehyde, caproaldehyde, enanthaldehyde, nonaldehyde, cyclobutyaldehyde, cyclopentylaldehyde, cyclohexylaldehyde, furfural, 2-thiophenealdehyde, 2-pyrrolealdehyde, imidazolealdehyde, oxazolealdehyde, pyridylaldehyde, pyrimidylaldehyde, 3-indolealdehyde, malonic acid half aldehyde and a mono aldehyde derivative of a dicarboxylic acid.

13. A process according to claim 2 wherein the hydantoin formed has the formula

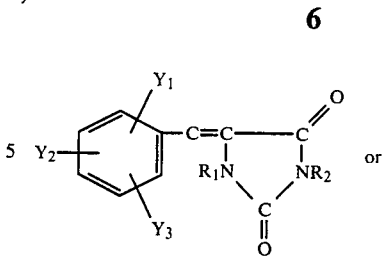

or

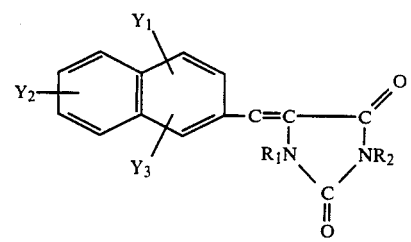

wherein $R_1$ and $R_2$ are hydrogen, alkyl, aryl, or amino and the aldehyde employed has the formula

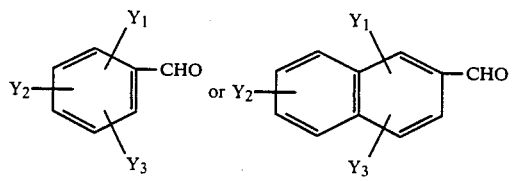

where $Y_1$, $Y_2$, and $Y_3$ are hydrogen, alkyl, alkenyl, cycloalkyl, cycloalkenyl, aryl, halogen, hydroxy, nitro, amino, alkylaminoalkyl, dialkylaminoalkyl, alkoxy, haloalkyl, haloalkenyl, alkylthio, acyloxy, acylthio, alkaryl, aralkyl, acylaminoalkyl, cycloalkyl having a —CH$_2$— group replaced by —O—, —S—, or —NH—, cycloalkenyl having a —CH$_2$— replaced by —N— or where two of the members $Y_1$, $Y_2$ and $Y_3$ are joined together to form an alkylene group or an alkenylene group having at least one CH$_2$ group replaced by —O—, —S—, or —NH— or an alkenylene group having at least one —CH= group replaced by —N=.

14. A process according to claim 13 wherein the aldehyde employed is selected from the group consisting of benzaldehyde, tolylaldehyde, 4-isopropylbenzaldehyde, 4-hydroxybenzaldehyde, 3,4,5-trimethoxybenzaldehyde, 3-bromo-4-methoxybenzaldehyde, 3,4-methylenedioxybenzaldehyde, 2-hydroxy-4-nitrobenzaldehyde, 4,5-dimethoxy-2-nitrobenzaldehyde, salicylaldehyde, vanillin, 4-phenylbenzaldehyde, 4-benzylbenzaldehyde, 4-fluorobenzaldehyde, 4-dimethylaminobenzaldehyde, 4-acetoxybenzaldehyde, 4-acetaminobenzaldehyde, 4-methylthiobenzaldehyde, and 3,5-dichloro-4-hydroxybenzaldehyde, p-tolylaldehyde, m-tolylaldehyde, 4-chlorobenzaldehyde, 4-hexylbenzaldehyde, 2-allylbenzaldehyde, 4-allylbenzaldehyde, 2-vinylbenzaldehyde, 3-vinylbenzaldehyde, 4-methallylbenzaldehyde, 4-crotylbenzaldehyde, 2-nitrobenzaldehyde, 3-nitrobenzaldehyde, 4-nitrobenzaldehyde, 2-aminobenzaldehyde, 4-aminobenzaldehyde, 4-cyclopropylbenzaldehyde, 2-cyclopropylbenzaldehyde, 4-cyclohexylbenzaldehyde, 2,6-dichlorobenzaldehyde, anisaldehyde, 3-hydroxybenzaldehyde, 2-hydroxybenzaldehyde, 2-hydroxy-4-methylbenzaldehyde, 2-hydroxy-3-methoxybenzaldehyde, veratraldehyde, 2,4-dihydroxybenzaldehyde, 2,5-dihydroxybenzaldehyde, 4-cyclohexenylbenzaldehyde, 4-cyclooctylbenzaldehyde, 4-piperidinylbenzaldehyde, 4-pyridinebenzaldehyde, 4-furylbenzaldehyde, 4-thienylbenzaldehyde, 4-phenylethylbenzaldehyde, 4-sec.butylbenzaldehyde, 4-morpholinobenzaldehyde, 4-isopropoxybenzaldehyde, 2-propoxybenzaldehyde, 3-ethoxybenzaldehyde, 4-hexoxybenzaldehyde, 2-isopropylaminobenzaldehyde, 4-hexylaminobenzaldehyde, 4-diethylaminobenzaldehyde, 4-dipropylaminobenzaldehyde, 4-methylethylaminobenzaldehyde, 3,4-ethylenedioxybenzaldehyde, 4-acetylthiobenzaldehyde, 4-propionoxybenzaldehyde, 4-formoxybenzaldehyde, 4-butyroxybenzaldehyde, 3,4-tetramethylenebenzaldehyde, 3,4-trimethylenebenzaldehyde, 3,4-dihydroxybenzaldehyde, 3-indolecarboxyaldehyde.

15. A process according to claim 14 wherein the aldehyde employed is benzaldehyde.

* * * * *

UNITED STATES PATENT AND TRADEMARK OFFICE
CERTIFICATE OF CORRECTION

PATENT NO. : 4,582,903
DATED : April 15, 1986
INVENTOR(S) : Stanley B. Mirviss

It is certified that error appears in the above—identified patent and that said Letters Patent is hereby corrected as shown below:

Col. 2, line 66, "nonaldehyde" should be -- nonylaldehyde --.

Col. 3, line 44, "3-indenecarboxaldehyde" should be --3-indenecarboxyaldehyde--.

Col. 5, line 61, "nonaldehyde" should be -- nonylaldehyde --.

Signed and Sealed this

Nineteenth Day of August 1986

[SEAL]

Attest:

DONALD J. QUIGG

Attesting Officer

Commissioner of Patents and Trademarks